US007060050B2

(12) United States Patent
Kliem et al.

(10) Patent No.: US 7,060,050 B2

(45) Date of Patent: Jun. 13, 2006

(54) BUTTON-BALLOON SYSTEM

(75) Inventors: Michael Kliem, Aurachtal-Falkendorf (DE); Reinhold Wolkenstörfer, Neunkirchen (DE); Harry Kleijs, Erlangen-Eltersdorf (DE)

(73) Assignee: Nutricia Healthcare S.A. (CH)

(*) Notice: Subject to any disclaimer, the term of this patent is extended or adjusted under 35 U.S.C. 154(b) by 0 days.

(21) Appl. No.: 10/475,528

(22) PCT Filed: Apr. 30, 2002

(86) PCT No.: PCT/EP02/04772

§ 371 (c)(1), (2), (4) Date: Mar. 16, 2004

(87) PCT Pub. No.: WO02/087492

PCT Pub. Date: Nov. 7, 2002

(65) Prior Publication Data

US 2004/0147874 A1 Jul. 29, 2004

(30) Foreign Application Priority Data

Apr. 30, 2001 (DE) ................................ 101 21 170
Jun. 28, 2001 (DE) ................................ 101 31 152

(51) Int. Cl.
*A61M 29/00* (2006.01)

(52) U.S. Cl. ................... 604/96.01; 604/910; 604/264; 604/104

(58) Field of Classification Search ................ 604/525, 604/103.07, 96.01, 103.06, 910, 174, 175, 604/524, 523, 104–105, 264
See application file for complete search history.

(56) References Cited

U.S. PATENT DOCUMENTS

| | | | | |
|---|---|---|---|---|
| 3,915,171 | A | | 10/1975 | Shermeta |
| 4,479,497 | A | * | 10/1984 | Fogarty et al. ............. 606/194 |
| 4,666,433 | A | * | 5/1987 | Parks .......................... 604/178 |
| 5,125,897 | A | * | 6/1992 | Quinn et al. ............. 604/99.03 |
| 5,399,173 | A | * | 3/1995 | Parks et al. ................. 604/533 |
| 5,531,719 | A | * | 7/1996 | Takahashi ................... 604/525 |
| 5,556,385 | A | * | 9/1996 | Andersen .................... 604/174 |
| 5,613,947 | A | * | 3/1997 | Chin ..................... 604/103.13 |
| 5,632,735 | A | * | 5/1997 | Wyatt et al. ................ 604/539 |
| 5,709,874 | A | * | 1/1998 | Hanson et al. .............. 424/423 |
| 5,997,503 | A | | 12/1999 | Christian et al. |
| 5,997,546 | A | * | 12/1999 | Foster et al. ................ 606/108 |
| 6,010,479 | A | * | 1/2000 | Dimitri .................... 604/96.01 |

(Continued)

FOREIGN PATENT DOCUMENTS

EP 0 729 761 9/1996

(Continued)

*Primary Examiner*—Nicholas Lucchesi
*Assistant Examiner*—Theodore J. Stigell
(74) *Attorney, Agent, or Firm*—Bacon & Thomas PLLC

(57) ABSTRACT

A balloon-button system or a catheter for performing percutaneous enteral feeding includes a holding part, which can be placed on the abdominal wall, and a probe tube, which extends from the holding part while being connected thereto and via which the nourishment that is inserted through a connecting part situated in the holding part can be introduced into the stomach lumen. A distal end of the probe tube is turned inside out and pulled back over the probe tube and joined in a fluid tight manner to form a single-piece probe tube having an inner and an outer tube portion wherein the outer tube is expandable to form a balloon by introducing a fluid. This system is characterized in that the probe tube surrounds a protective tube, and the protective tube has a higher Shore A hardness than the probe tube.

13 Claims, 5 Drawing Sheets

U.S. PATENT DOCUMENTS 6,066,112 A 5/2000 Quinn
6,488,654 B1 * 12/2002 Gonzalez et al. ...... 604/103.06
6,508,784 B1 * 1/2003 Shu ......................... 604/96.01
6,582,388 B1 * 6/2003 Coleman et al. ............... 604/8
6,695,831 B1 * 2/2004 Tsukada et al. ............. 604/544
6,767,340 B1 * 7/2004 Willis et al. ................ 604/256
2004/0106900 A1 * 6/2004 Triebes et al. .............. 604/104

FOREIGN PATENT DOCUMENTS

WO WO 95 04564 2/1995

* cited by examiner

BUTTON-BALLOON SYSTEM

CROSS REFERENCE TO RELATED APPLICATIONS

This application is the national stage of PCT/EP02/04772, filed Apr. 30, 2002, which claims the benefit of priority of German application 101 21 170.8, filed Apr. 30, 2001, and German application 101 31 152.4, filed Jun. 28, 2001.

FIELD OF THE INVENTION

The invention relates to a balloon-button system or a catheter for performing percutaneous enteral feeding, comprising a holding part, which can be placed on the abdominal wall, and a probe tube, which extends from the holding part while being connected thereto and via which the nourishment that is inserted through a connecting part situated in the holding part can be introduced into the stomach lumen, with the probe tube comprising an inner tube and an outer tube that surrounds the same, and the outer tube being formed by turning the inner tube inside out at the distal end of the latter and by pulling it back, and being joined, at its proximal end, to the inner tube in a fluid-tight manner, and being expandable to form a balloon by introducing water or the like via a supply line, which extends from the holding part and which opens out between the outer tube and the inner tube.

BACKGROUND

Enteral feeding by applying a percutaneous endoscopic gastrostomy (PEG) is methodically safe and clinically established (Dormann, A. J., et al. Am J Gastroenterol 1999).

Moreover, so-called button systems are known, which are protected against slipping out by means of a balloon or a flexible sleeve. After introducing the probe tube of such a button system through the stoma into the stomach, the balloon is filled from outside via a valve with a liquid, or the sleeve is relieved. During filling, the balloon expands or the sleeve deploys its final shape. The thereby formed retaining member fixes the system at the distal end. The button system is thereby supported by a holding part outside on the abdominal wall. Usually, water is used as the liquid for deploying the balloon.

In the known anterior balloon-button systems, the probe tube is surrounded by an outer tube resting against it at the outside. The outer tube is joined to the probe tube, e.g. bonded by adhesive, both on its distal and proximal end. If water or the like is then introduced into the interspace between the outer tube and the probe tube (to be more precise, between the inner surface area of the outer tube and the outer surface area of the probe tube), the outer tube will assume a balloon-like shape. In order to enable this, the outer tube must be made of a material having a sufficiently high degree of flexibility, e.g. of silicone.

The weak points of this known balloon-button system are the connection points or bonding locations between the outer tube and the probe tube, which forms the inner tube in that section where it is surrounded by the outer tube. These connection or seam locations turned out not to support a permanent load so that water from the balloon could reach the stomach, and the safe fit of the system could no longer be guaranteed.

In order to encounter the described drawback, balloon-button systems have been developed, wherein the probe tube and the outer tube are manufactured in one piece. Such a tube is obtained in that the distal end of the probe tube is turned inside out and is returned or pulled up over the distal end of the then resulting inner tube. In this manner, the distal connection of the inner tube and the outer tube can be formed in one piece. However, the outer tube, now as before, must be connected at its proximal end to the inner tube by bonding or the like.

These systems are insofar disadvantageous as the inner tube and the outer tube, due to their one-piece configuration, must be manufactured from the same material. In other words, the inner tube and the outer tube have the same flexibility. It has turned out to be difficult to use a kind of mean flexibility so that, on the one hand, the outer tube is sufficiently flexible to form a balloon, and the inner tube, on the other hand, has sufficient and required stability. This applies even then when the wall thickness of the probe tube varies along its axial length.

Button systems are already known wherein the balloon is comprised of differently configured retaining members, e.g. sleeves. In this respect, reference is made to EP-A-0 824 929 and the therein mentioned documents U.S. Pat. No. 3,108,595 and U.S. Pat. No. 4,666,433.

BRIEF SUMMARY OF THE INVENTION

It is the object of the present invention to provide a balloon-button system, the probe tube of which has sufficient stability, and the outer tube of which that forms the balloon has sufficient flexibility and is permanently and securely connected to the probe tube.

This object is achieved by a balloon-button system according to the teaching of claim 1.

The probe tube of the balloon-button system according to the invention is quasi a tube-in-tube system. The innermost tube is formed by a so-called support tube that is enclosed over its entire length by a further tube (this further tube here will be referred to as a probe tube for simplicity reasons). This probe tube is turned inside out at its distal end. The area turned inside out thus is pulled over or returned over this probe tube from the distal end in the direction towards the holding part. This further tube or probe tube, in the area of the distal end of the probe tube, hence forms an outer tube as well as an inner tube. For reasons of simple terminology, the probe tube in the latter area is also referred to as an inner tube, while its area turned inside out is referred to as an outer tube. This probe tube, however, is comprised of one piece. The inner tube, at its distal end, hence transits into the outer tube in one piece. In other words, the probe tube has no adhesive joint or the like at its distal end. Of course, the outer tube, at its proximal end, must be connected to the inner tube in the usual way by adhesive bonding or the like in a fluid-tight manner.

According to the invention, the support tube enclosed by the probe tube has a higher Shore A hardness than the probe tube. Thus, it is possible to impart the material that is expanded to form a balloon, the flexibility required for this purpose. Furthermore, the tube unit introduced into the stoma and the stomach has a sufficient stability and rigidity due to the higher Shore A hardness of the support tube.

According to a preferred embodiment, the support tube has a Shore A hardness of 65 to 100, and in particular of about 80, whereas the probe tube has a Shore A hardness of 20 to 55, and in particular of about 40.

By the range indication of 65 to 100 and also 20 to 55, all intermediate values and especially all intermediate single values are included and disclosed. The range for the Shore A hardness of 65 to 100 hence includes at least the following single values:

65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100.

The same applies for the Shore A hardness of 20 to 55; this range, too, includes at least all single values and hence the values:

20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 and 55.

Moreover, all closer ranges between the end values of the range indications are also included and disclosed. Thus, the range of 65 to 100, for example, is inter alia representative of 70–100, 75–100, 80–100, 85–100, and 90–100, as well as 65–95, 65–90; 65–85, 65–80 and 65–75, as well as of the ranges 70–95 and 75–90, so as to mention only a few. Also, the range of 20–55 includes all closer ranges, and in particular, for example, 20–50, 20–45, 20–35, 20–30, 25–55, 30–55, 35–55, 40–55, 25–50 und 30–45.

The material of which both the support tube and the probe tube are manufactured preferably is an injection-moldable material, e.g. a rubber, and, particularly preferred, silicone.

For manufacturing the probe tube, it is useful to manufacture and in particular injection-mold the inner support tube first. Subsequently, this support tube is surrounded by the material forming the probe tube, and in particular the silicone material, with the probe tube extending beyond the distal end of the support tube. Following the distal end of this probe tube is that tube portion or that material that will constitute the outer tube in that this tube portion or material is returned to the probe tube or is turned inside out. The wall thickness of this outer tube, related to the returned state or the state turned inside out, is smaller at the distal end than at the proximal end. The wall thickness thereby may be increased continuously or discontinuously. Thus, it is achieved that the outer tube has a smaller thickness at its distal end (related to the state turned inside out) than at its proximal end, and hence is more flexible near its distal end, which will be explained later in more detail.

In the transition area from the inner tube to the outer tube, the inner tube preferably is tapered towards the outer tube, whereas the outer tube in turn then is expanded in a funnel-shape in the direction towards its proximal end. These indications thereby relate to the non-inflated state. In other words, a kind of constriction oriented radially inwards is present at the transition from the inner tube to the outer tube. If the outer tube is turned inside out and pulled back over the inner tube, then the probe tube, at its free end with which it is introduced, is acutely tapered off, whereby this introduction is facilitated.

Also, the holding part which is placed on a patient's abdominal wall, preferably is a holding part, also referred to as a silicone holding part in the following, which is manufactured by injection-molding of silicone. In order to guarantee a permanent connection between the probe tube and the silicone holding part, the proximal end of the probe tube, that preferably has been manufactured separately in advance, is surrounded by injection material of this silicone holding part during the injection-molding process of the silicone holding part, so that a permanent connection is given. It is also possible to manufacture the holding part and the probe tube in one operation, e.g. by injection-molding.

Like any other balloon-button system hitherto known, the holding part of the system of the invention, too, features a connecting part which is approximately tubular or funnel-shaped. It may be, for example, a connection piece similar to a Luer lock. This connecting part appropriately is comprised of a hard plastic part that is surrounded, during the manufacture process of the silicone holding part, by the silicone material serving for manufacturing the holding part.

For improving the connection between this hard plastic connecting part and the remainder of the silicone holding part, the connecting part preferably features a rim protruding radially outwards and being at least in part peripherally circumferential, and having at least one break-through. When this connecting part is surrounded with silicone material during the injection-molding process, the silicone material not only penetrates into and fills the break-through, but also encloses the rim, so that pulling out of the connecting part in the axial direction is prevented or at least aggravated due to the form-fit enclosure of this rim by the silicone material.

In order to obtain a kind of twist protection of the connecting part relative to the rest of the holding part, the connecting part moreover preferably features several knobs or ribs oriented radially outwards either attached to the connecting part as such and/or to the lower side of the rim or formed in one piece with same, with the lower side of the rim being that side that points towards the probe tube.

BRIEF DESCRIPTION OF THE DRAWINGS

The invention will be explained in more detail by means of the accompanying drawings illustrating preferred embodiments. The drawings show.

Figure 1:
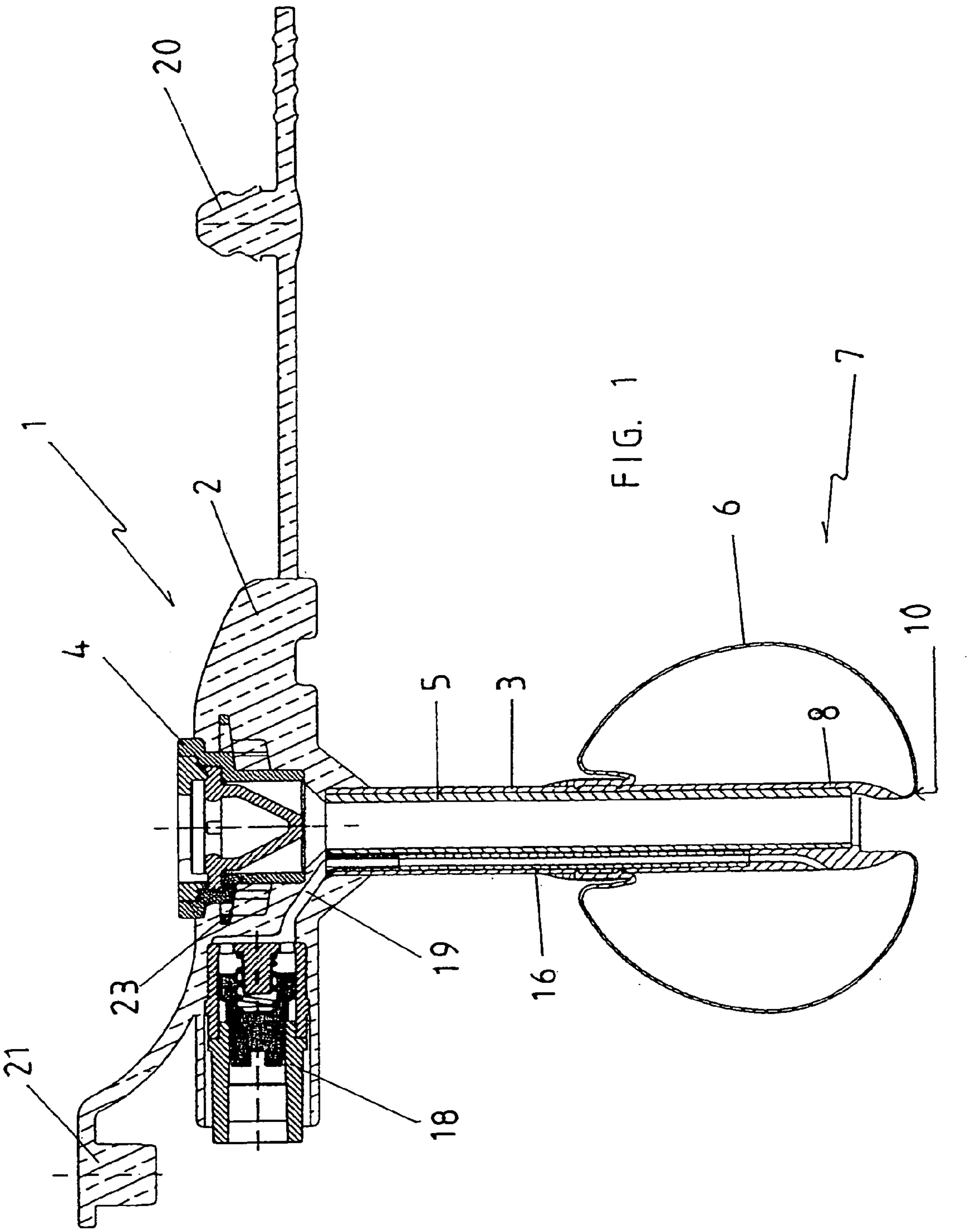
FIG. 1 a longitudinal section through the balloon-button system according to the invention with the balloon filled, FIG. 2 a section view analogous to FIG. 1, wherein, however, some parts have been omitted for better representation, and with the balloon emptied, FIG. 3 a longitudinal section view of the probe tube of the balloon-button system according to the invention, FIG. 4 a cross-sectional view taken along line B—B of FIG. 3, FIG. 5 a longitudinal section view analogous to FIG. 3, with the probe tube, however, being turned inside out, FIG. 6 an enlarged view of the area A of FIG. 5, FIG. 7 a side view of a connecting part, FIG. 8 a cross-sectional view of the connecting part shown in FIG. 7, and FIG. 9 a top view from above of the connecting part shown in FIG. 7.

The balloon-button system 1 shown in a longitudinal section view in FIG. 1 or the catheter shown there for performing percutaneous enteral feeding has a holding part 2 connected to a probe tube 3. The holding part 2 is injection-molded from silicone and encloses a connecting part 4 constituting a connection similar to a Luer lock, and through which a nutrient solution etc. may be introduced into the probe tube 3 in the usual manner by means of known pass-over tubes (not shown). For this purpose, the probe tube 3 is introduced in a patient's stoma in such a manner that the probe tube 3 reaches the stomach and the holding part 2 rests on the abdominal wall. When the system is fixed in place, which will be explained later in more detail, the nutrient solution or similar may be applied through this system. The nutrient solution then exits at the free distal end 10 of the probe tube and reaches the stomach.

DETAILED DESCRIPTION OF THE INVENTION

The balloon 7 shown in FIG. 1 serves for fixing system 1 in place, which balloon is formed in the distal end area of the probe tube 3, which will be explained later in more detail.

At the proximal end, the probe tube 3 is enclosed by the silicone material of holding part 2. For manufacturing this system, the probe tube 3 is first manufactured separately, and then the silicone holding part 2 is added by molding.

Figure 3:
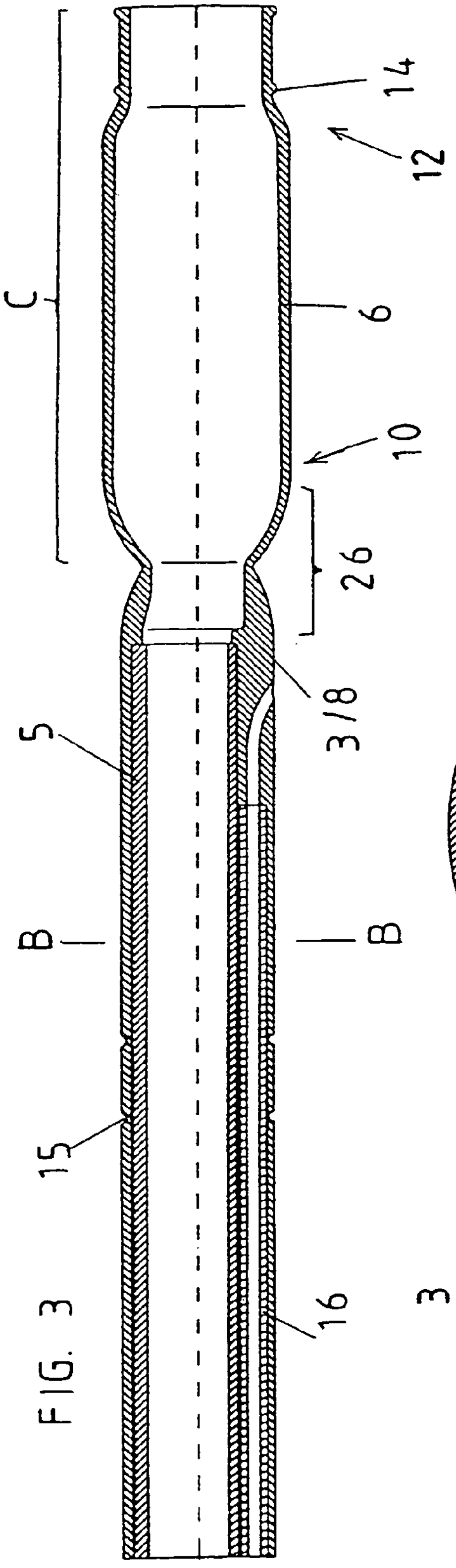
Figure 4:
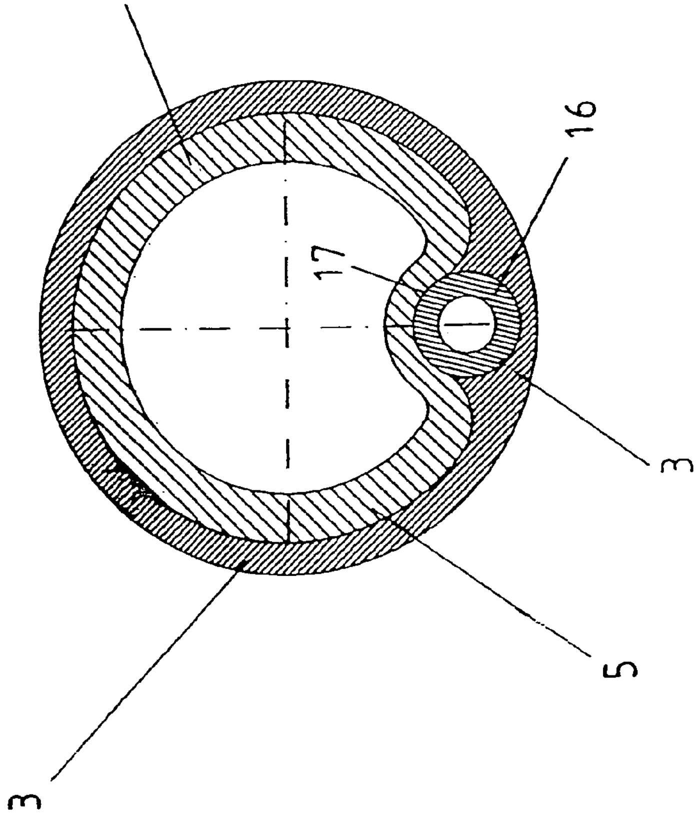

For manufacturing the probe tube 3, a tube of the kind shown in FIG. 3 is made, e.g. by injection-molding. The probe tube 3 shown there comprises a support tube 5 that has a higher Shore A hardness than probe tube 3.

After manufacturing support tube 5, e.g. by injection molding of silicone, this support tube 5 is surrounded by the silicone material forming probe tube 3. As a result, probe tube 3 extends beyond the distal end of support tube 5.

Figure 5:
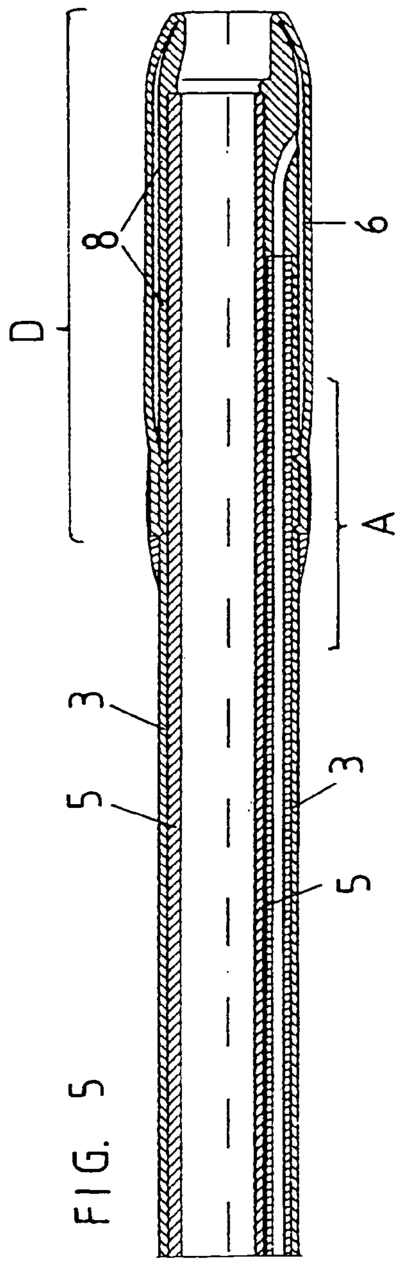

The end portion of probe tube 3 designated C in FIG. 3 is turned inside out and is again pulled over or returned on probe tube 3. The then resulting situation is illustrated in FIG. 5. The pulled back area of probe tube 3 represents the outer tube 6 in area D.

The end portion of probe tube 3 designated C in FIG. 3 hence serves for forming the outer tube 6. The inner diameter of this end portion C, in that case, corresponds to a high degree to or is slightly smaller than the outer diameter of probe tube 3 in that area, over which this end portion C is intended to be pulled by a return operation or by turning it inside out. At the proximal end 12 (related to the state turned inside out), this end portion C is tapered or its inner diameter is smaller. This tapered area of end portion C is shown at the right end in FIG. 3. This tapered portion serves the purpose of establishing the connection to the probe tube when this end portion C is turned inside out. This tapered area hence is intended not to expand during inflation of the balloon, but is intended to rest against the outer surface area of probe tube 3, such as it is shown, for example, in FIG. 1.

The area of end portion C having the larger inner diameter serves the purpose of forming the outer tube 6 (after turning the inside out), and constitutes the area that can be inflated to form a balloon.

Figure 6:
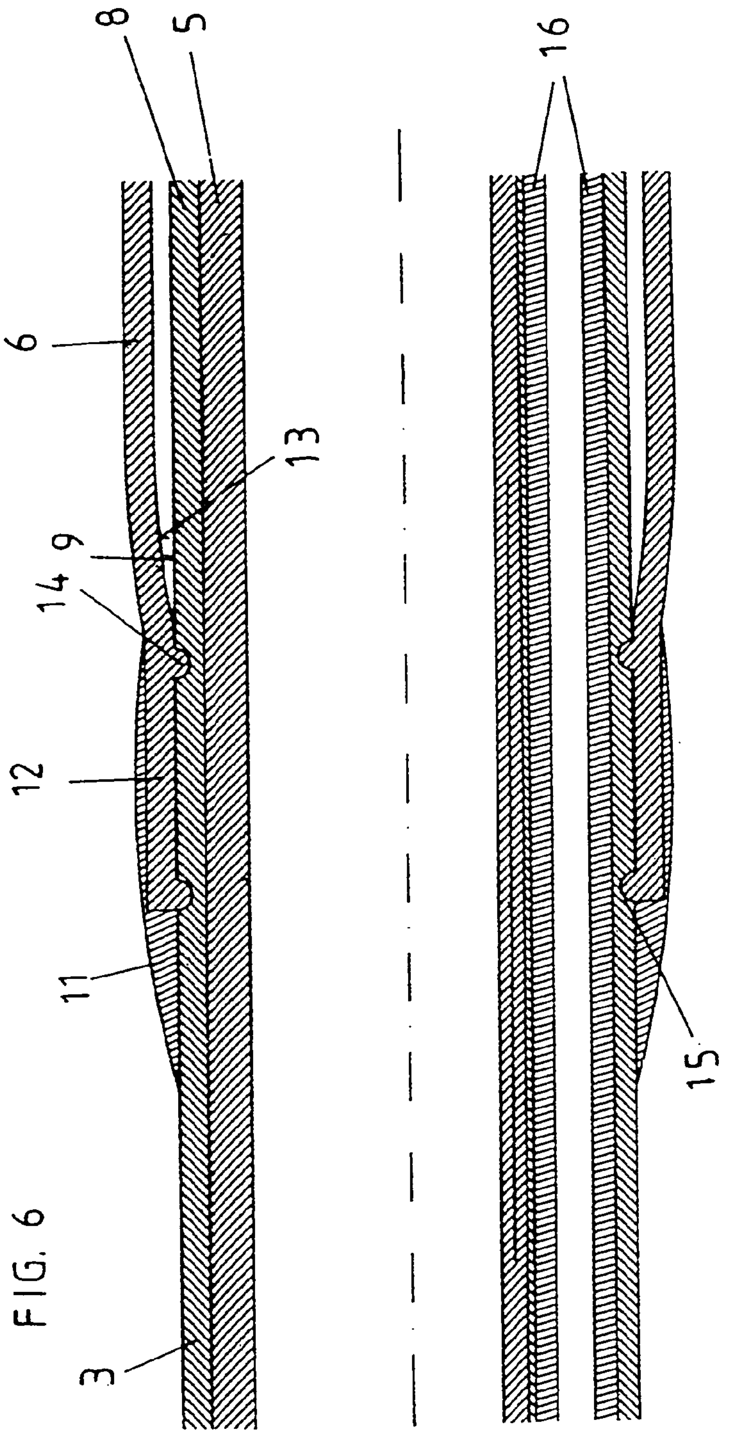
Figure 8:
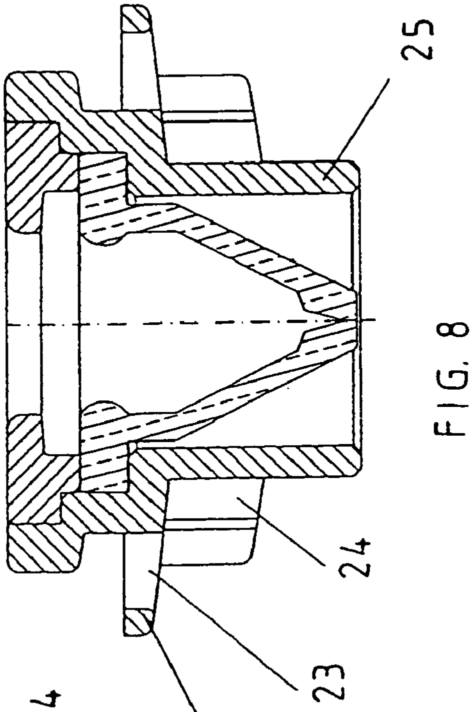

The wall thickness of the outer tube 6, in that case, is continuously increased from its distal end 10 towards its proximal end 12. Thus, the wall thickness of the outer tube is smaller in the vicinity of the distal end 10 than in the vicinity of the proximal end 12. Thereby, during inflation, the balloon or outer tube 6 expands more near the distal end 10 than it does near the proximal end 12. This leads to the effect that outer tube 6, during inflation, folds back about the connection area at its distal end 10, which connection area is bonded with probe tube 3, and hence also folds back about sleeve 11, from the position shown in FIG. 6 to the position shown in FIG. 1, and hence rests externally against this connection area and forms a kind of additional sleeve. Due to the pressure prevailing inside of balloon 7, the outer tube 6, in addition, is pressed again radially inside to probe tube 3 (to be more precise, to sleeve 11) and the proximal end 12 thereof, resulting in an additional protection of this connection area.

In the transition area 26 (FIG. 3), the outer diameter of the inner tube 8 is decreased towards the outer tube 6. Thereby, the inner tube 8 is tapered in this transition area 26 towards the outer tube 6. The outer tube 6 then expands again in a funnel-shape, starting from the inner tube towards its proximal end 12, and then passes over into a continuous area, that remains approximately constant up to the tapered area described above.

Figure 2:
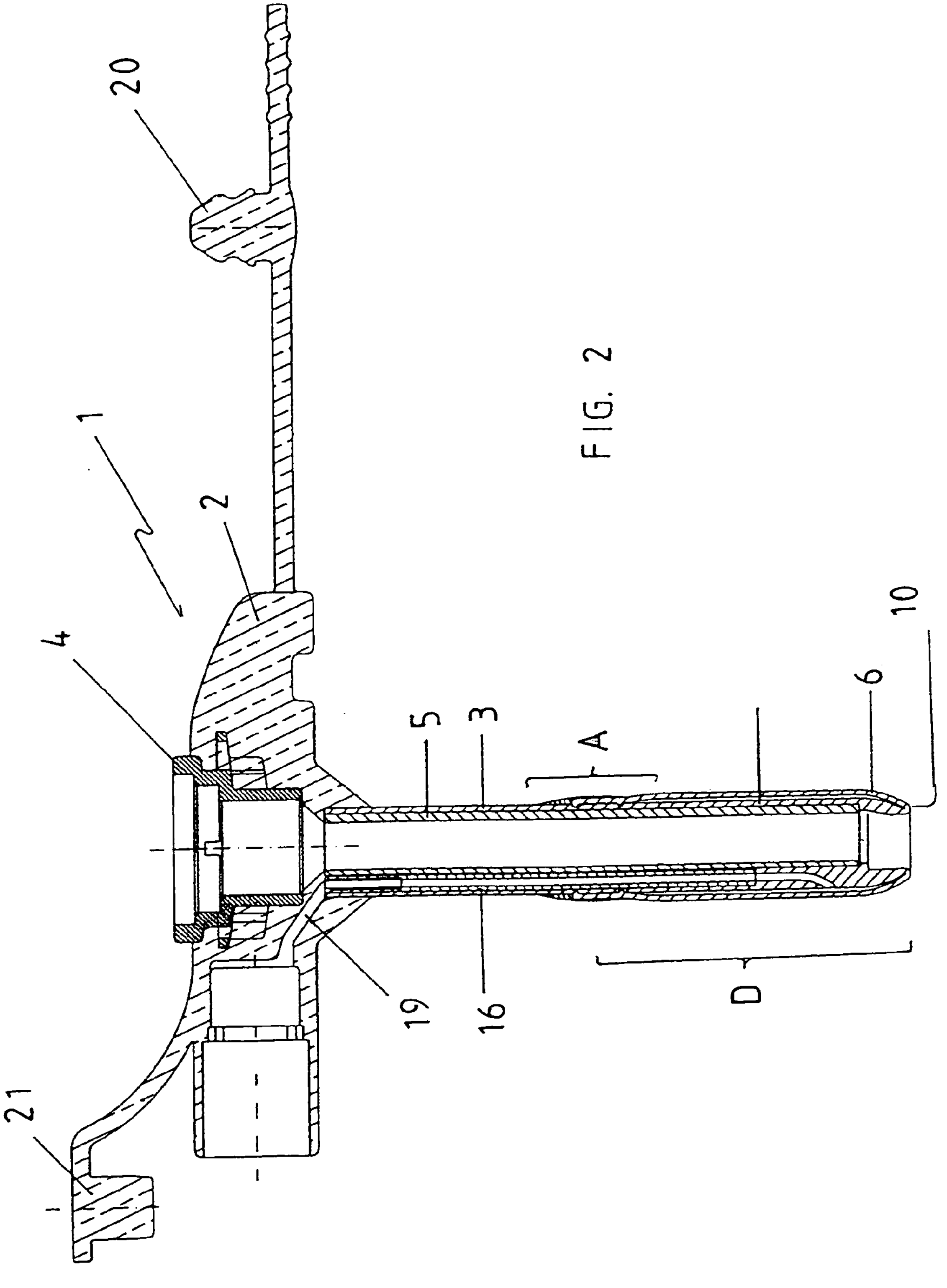

This results in the formation of a kind of constriction. When the outer tube 6 is turned inside out, then the inner tube, together with the outer tube 6 nested over same, forms at its free end a kind of acutely tapered end such as it is shown, for example, in FIG. 5 and also in FIG. 2. This facilitates the introduction of the probe tube.

At its proximal end 12, the outer tube 6 has on its inner surface area 13 peripherally circumferential beads 14 that engage in grooves 15 formed in the outer surface area 9 of probe tube 3. Moreover, probe tube 3 and outer tube 6 are bonded together in this area A. In addition, this entire portion is enclosed by a sleeve 11 such as it is in particular shown in FIG. 6. This sleeve 11, too, is bonded together with those parts which are enclosed by sleeve 11.

The probe tube 3 or inner tube 8 hence is formed in one piece with the outer tube 6, and, to be more precise, of silicone having a Shore A hardness of about 40 in the embodiment shown. The support tube 5 in that case has a Shore A hardness of about 80.

Due to this configuration, a kind of loop, such as it is shown in FIG. 5, results at the distal end 10 at the transition between probe tube 3 or inner tube 8 and outer tube 6. Therefore, a reliable connection is given in this location or in this area, which is of a permanent and dependable nature.

Into probe tube 3, a supply line in the form of a supply tube 16 is integrated, which extends in the axial direction and which is quasi inserted between probe tube 3 and support tube 5. For this purpose, support tube 5 has an axially extending, approximately U-shaped groove, in which this supply line or this supply tube is 16 inserted. On the outside, this supply tube 16 is surrounded by the probe tube material. This supply tube 16 exits probe tube 3 in region D, to be more precise, in the distal end area D thereof. Through this supply tube 16, water can be introduced from the holding part 2 into the space between the outer tube 6 and the inner tube 8 in area D. The state, which may hereby be obtained, is shown in FIG. 1.

Situated in holding part 2 is a valve 18 of the usual kind, via which water may be introduced into supply tube 16 through a feed line 19 formed in holding part 2.

Holding part 2, moreover, is provided with a plug 20 for closing the connecting part 4, and with a plug 21 for closing valve 18. These plugs 20 and 21 are connected to the central area of holding part 2 by means of a flexible area.

When water is filled in the area D between the outer tube 6 and the inner tube 3, the outer tube 6 folds back at its proximal end 12 towards holding part 2, so that the shape results which is shown in FIG. 1, since the outer tube 6 is made of a flexible material, so that also the wall of outer tube 6 becomes longer during the "inflation" of balloon 7 and enables this folding back.

Figure 7:
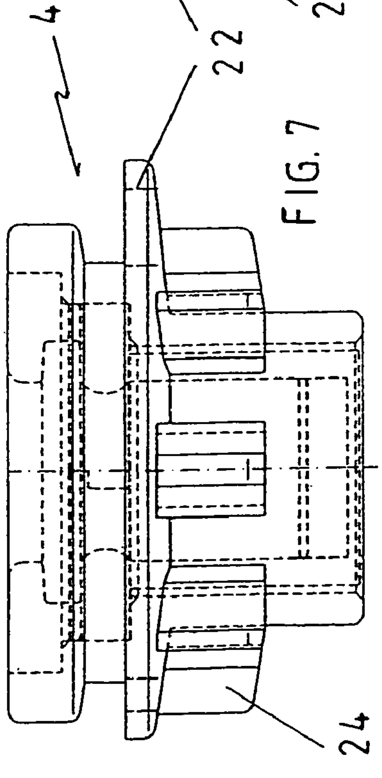
Figure 9:
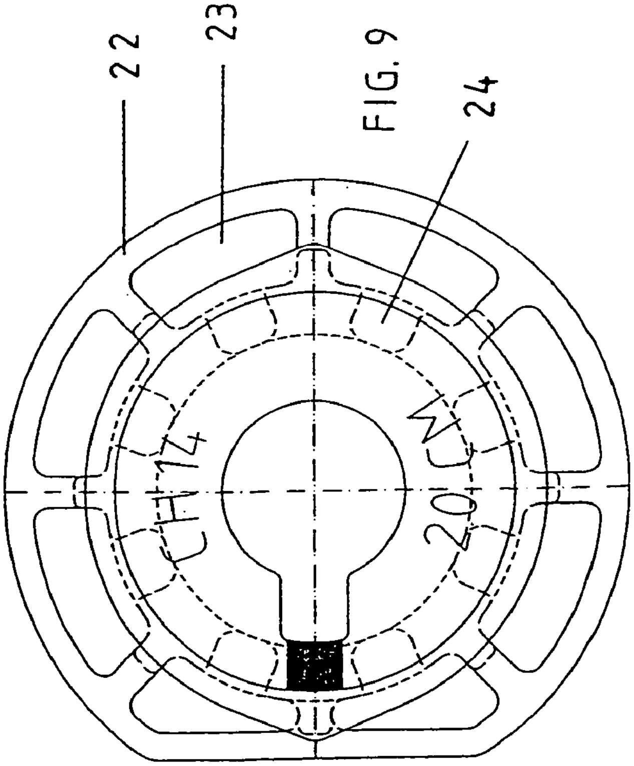

The connecting part 4 shown in FIG. 7 in a side view has a peripherally circumferential rim 22 with several breakthroughs 23 filled with the silicone material of holding part 2. Rim 22 in that case is injection-molded in one piece with the rest of connecting part 4, and, to be more precise, of a hard plastic material.

At the axial side of rim 22 pointing towards probe tube 3, several knobs 24 or ribs are integrally molded, which are at the same time integrally molded at the tubular area 25 of connecting part 4 and extend radially outwards from there. Thereby, an axial locking and a twist protection of connecting part 4 is guaranteed.

Due to the higher Shore A hardness of support tube 5, the balloon-button system of the invention or the catheter of the invention has sufficient stability and rigidity. At the same time and due to the comparatively lower Shore A hardness of probe tube 3 and also of outer tube 6, sufficient flexibility is given for the material forming balloon 7. The connection between the outer tube and probe tube at the distal end is in one piece and hence of a particularly reliable nature. Due to the shape and configuration of the balloon when it is filled with water, a safe fit of the system of the invention is ensured.

LIST OF REFERENCE NUMERALS

1 system
2 holding part
3 probe tube
4 connecting part
5 support tube
6 outer tube
7 balloon
8 inner tube
9 outer surface area
10 free or distal end of probe tube 3
11 sleeve
12 proximal end of outer tube 6
13 inner surface area
14 bead
15 peripherally circumferential groove
16 supply line or supply tube
17 axial groove
18 valve
19 feed line
20 plug for connecting part 4
21 plug for valve 18
22 rim
23 break-through
24 knobs
25 tubular area of connecting part
26 transition area

The invention claimed is:

1. A balloon-button system for performing percutaneous enteral feeding, comprising a holding part, which can be placed on the abdominal wall, and a probe tube connected to and extending from the holding part via which nourishment that is inserted through a connecting part situated in the holding part can be introduced into the stomach lumen, wherein a distal end of the probe tube is turned inside out over a portion of the probe tube proximal to the distal end, and the distal end joined to the probe tube in a fluid-tight manner to define an outer tube overlying an inner tube, the distal end of the probe tube being a proximal end of the outer tube, the probe tube, outer tube, and inner tube being a single monolithic piece;

wherein the outer tube is expandable to form a balloon by introducing water or the like via a supply line which extends from the holding part and which opens out between the outer tube and the inner tube, and wherein the probe tube encloses a support tube, and the support tube has a higher Shore A hardness than probe tube.

2. The balloon-button system according to claim 1, wherein the support tube has a Shore A hardness of 65 to 100, and the probe tube has a Shore A hardness of 20 to 55.

3. The balloon-button system according to claim 2, wherein the support tube has a Shore A hardness of about 80, and the probe tube has a Shore A hardness of about 40.

4. The balloon-button system according to claim 1, wherein the outer tube, at its proximal end, where it is connected to said probe tube, has at least one peripherally circumferential bead on its inner surface area, which bead engages into an opposite groove formed in the outer surface area of said inner tube.

5. The balloon-button system according claim 1, wherein the outer tube, at its proximal end is connected to the probe tube by bonding.

6. The balloon-button system according to claim 1, wherein the probe tube and the support tube are made of an injection-moldable material.

7. The balloon-button system according to claim 6, wherein the injection-moldable material is silicone.

8. The balloon-button system according to claim 1, wherein, the wall thickness of the outer tube is smaller in the area of its distal end than in the area of its proximal end.

9. The balloon-button system according to claim 1, wherein, said inner tube is tapered in a transition area towards said outer tube, and said outer tube, in this transition area again is expanded in a funnel-shape in a direction towards its proximal end.

10. The balloon-button system according to claim 1, wherein, the holding part is a silicone holding part made by injection-molding of silicone.

11. The balloon-button system according to claim 10, wherein the connection between the probe tube and the silicone holding part is manufactured by surrounding the proximal end of the probe tube with silicone material during injection-molding of the silicone holding part.

12. The balloon-button system according to claim 10, wherein the connecting part is approximately tubular or funnel-shaped, is made of hard plastic, and has a radially outwardly protruding and at least in part peripherally circumferential rim, which has at least one break-through, and which is completely surrounded by the silicone holding part.

13. The balloon-button system according to claim 12, wherein the connecting part, on the lower side of said rim and hence on the side pointing towards the probe tube has several knobs oriented radially outwards, which either are attached to said holding part and/or to the lower side of said rim and/or are formed in one piece with same and are surrounded by the silicone holding part.

* * * * *